United States Patent
Castillo-Welter et al.

(10) Patent No.: US 10,898,874 B2
(45) Date of Patent: Jan. 26, 2021

(54) REACTOR FOR CONDUCTING EXOTHERMIC EQUILIBRIUM REACTIONS

(71) Applicant: L'Air Liquide, Societe Anonyme pour l'Etude et l'Exploitation des Procedes Georges Claude, Paris (FR)

(72) Inventors: Frank Castillo-Welter, Friedrichsdorf (DE); Stephane Haag, Frankfurt am Main (DE); Robert Frind, Kreischa (DE); Timm Schuhmann, Offenbach (DE); Andreas Ochs, Bad Homburg (DE); Marc Wagner, Saint Maur des Fosses (FR); Solene Valentin, Le Pecq (FR)

(73) Assignee: L'Air Liquide Societe Anonyme Pour L'Etude Et L'Exploitation Des Procedes Georges Claude, Paris (FR)

( * ) Notice: Subject to any disclaimer, the term of this patent is extended or adjusted under 35 U.S.C. 154(b) by 0 days.

(21) Appl. No.: 16/612,631

(22) PCT Filed: Apr. 26, 2018

(86) PCT No.: PCT/EP2018/025129
§ 371 (c)(1),
(2) Date: Nov. 11, 2019

(87) PCT Pub. No.: WO2018/206153
PCT Pub. Date: Nov. 15, 2018

(65) Prior Publication Data
US 2020/0197890 A1 Jun. 25, 2020

(30) Foreign Application Priority Data
May 12, 2017 (EP) .................................. 17400024

(51) Int. Cl.
*B01J 8/04* (2006.01)
*C07C 29/152* (2006.01)
(Continued)

(52) U.S. Cl.
CPC ........... *B01J 8/0496* (2013.01); *B01J 8/0415* (2013.01); *B01J 8/0438* (2013.01); *B01J 8/0453* (2013.01);
(Continued)

(58) Field of Classification Search
CPC ...... B01J 8/0496; B01J 8/0438; B01J 8/0442; B01J 8/0484; B01J 8/0488; B01J 8/0492;
(Continued)

(56) References Cited

U.S. PATENT DOCUMENTS 4,326,041 A 4/1982 Bahnisch
5,631,302 A 5/1997 Konig et al.
(Continued)

FOREIGN PATENT DOCUMENTS

CN 106 380 376 2/2017
CN 106 518 609 3/2017
(Continued)

OTHER PUBLICATIONS

International Search Report and Written Report for PCT/EP2018/025131, dated Jun. 26, 2018.
(Continued)

*Primary Examiner* — Lessanework Seifu
(74) *Attorney, Agent, or Firm* — Justin K. Murray

(57) ABSTRACT

A reactor for conducting exothermic equilibrium reactions, especially for the performance of methanol synthesis by heterogeneously catalysed conversion of synthesis gas, is proposed, which enables readjustment and hence optimization of the reaction conditions along the longitudinal coordinate of the reactor. For this purpose, in accordance with the invention, the reactor is divided into a multitude of series-connected reaction cells, each of which comprises a preheating zone, a cooled reaction zone, one or more cooling zones and a deposition zone for condensable reaction prod- (Continued)

ucts. In this way, the reaction conditions are adjustable to the respective, local composition of the reaction mixture and variable over the reactor length.

17 Claims, 7 Drawing Sheets

(51) Int. Cl.
*B01J 8/06* (2006.01)
*C07C 31/04* (2006.01)
(52) U.S. Cl.
CPC .............. *B01J 8/067* (2013.01); *C07C 29/152* (2013.01); *B01J 2208/00141* (2013.01); *B01J 2208/00176* (2013.01); *B01J 2208/025* (2013.01); *B01J 2219/0002* (2013.01); *B01J 2219/0004* (2013.01); *C07C 31/04* (2013.01)
(58) Field of Classification Search
CPC .............. B01J 8/067; B01J 2208/00141; B01J 2208/0015; B01J 2208/00176; B01J 2208/025
See application file for complete search history.

(56) References Cited

U.S. PATENT DOCUMENTS

| | | | |
|---|---|---|---|
| 5,827,901 A | 10/1998 | Konig et al. | |
| 7,683,099 B2 | 3/2010 | Hipp | |
| 8,629,190 B2 | 1/2014 | Kopetsch | |
| 10,364,202 B2 | 7/2019 | Kopetsch et al. | |
| 2010/0280136 A1* | 11/2010 | Tonkovich | B01J 19/0093 |
| | | | 518/706 |
| 2016/0159714 A1 | 6/2016 | Zubrin et al. | |

FOREIGN PATENT DOCUMENTS

| | | |
|---|---|---|
| DE | 2 934 332 | 3/1981 |
| DE | 10 2008 049622 | 4/2010 |
| EP | 0 483 919 | 5/1992 |
| EP | 0 494 350 | 7/1992 |
| EP | 0 682 002 | 11/1995 |
| EP | 0 790 226 | 8/1997 |
| EP | 1 016 643 | 7/2000 |
| EP | 3 219 697 | 9/2017 |
| WO | WO 01/17936 | 3/2001 |
| WO | WO 2005/115607 | 12/2005 |
| WO | WO 2017/096699 | 8/2007 |
| WO | WO 2012/139703 | 10/2012 |
| WO | WO 2015/030578 | 3/2015 |
| WO | WO 2015/193440 | 12/2015 |

OTHER PUBLICATIONS

International Search Report and Written Opinion for PCT/EP2018/025129, dated Jul. 3, 2018.

Ullmann's Encyclopedia of Industrial Chemistry, Sixth Edition, 1998 Electronic Release, vol. 21, "Methanol" chapter, sub-chapter 5.2 "Synthesis," pp. 620-621.

\* cited by examiner

REACTOR FOR CONDUCTING EXOTHERMIC EQUILIBRIUM REACTIONS

CROSS REFERENCE TO RELATED APPLICATIONS

This application is a § 371 of International PCT Application PCT/EP2018/025129, filed Apr. 26, 2018, which claims the benefit of EP17400024.0, filed May 12, 2017, both of which are herein incorporated by reference in their entireties.

FIELD OF THE INVENTION

The invention relates to a reactor for conducting exothermic equilibrium reactions, in which a gaseous feed mixture is at least partly converted over a solid catalyst to a product mixture. One application example is the performance of methanol synthesis by heterogeneously catalysed conversion of synthesis gas comprising hydrogen and carbon oxides over solid catalysts.

BACKGROUND OF THE INVENTION

Reactors for performance of exothermic equilibrium reactions have long been known in the field. A reaction of this type which is of particular industrial importance is methanol synthesis by heterogeneously catalysed conversion of synthesis gas, i.e. mixtures of hydrogen and carbon oxides. Ullmann's Encyclopedia of Industrial Chemistry, Sixth Edition, 1998 Electronic Release, "Methanol" chapter, subchapter 5.2 "Synthesis", describes various basic processes for preparing methanol by catalytic conversion of synthesis gas comprising hydrogen and carbon oxides, in which such reactors are used.

A modern, two-stage process for preparing methanol is known, for example, from European patent specification EP 0 790 226 B1. The methanol is prepared in a cycle process in which a mixture of fresh and partly reacted synthesis gas is first fed to a water-cooled reactor and then to a gas-cooled reactor, in which the synthesis gas is converted in each case to methanol over a copper-based catalyst. The methanol prepared in the process is separated out of the synthesis gas to be recycled, which is then conducted through the gas-cooled reactor in countercurrent as coolant and is preheated to a temperature of 220 to 280° C., before it is introduced into the first synthesis reactor. A portion of the synthesis gas to be recycled is removed from the process as purge stream in order to prevent inert components from accumulating within the synthesis circuit. This measure is also taught in German published specification DE 2934332 A1 and European patent application EP 1016643 A1.

The main conversion of the synthesis gas (CO, CO2, H2) is typically achieved in the water-cooled reactor stage, and the majority of the heat of reaction is removed, while a nevertheless considerable proportion of the synthesis gas is converted under milder conditions in the gas-cooled stage.

In some plant configurations, an intermediate condensation stage is additionally provided between the two reaction stages, in order to reduce the proportion of reaction products formed (predominantly methanol and water) in the feed gas to the second reaction stage and hence to further increase the achievable conversion of the reactants. A plant configuration of this kind is taught, for example, in German patent specification DE 10 2008 049 622 B4.

The water-cooled reactor (WCR) is typically a tubular reactor having corresponding tube plates, in which the catalyst is introduced into the tubes, while the cooling is effected by means of boiling water or steam generation on the shell side around the tubes. In the gas-cooled reactor (GCR), the cooling is effected with the feed gas which is guided through the tubes and is heated on its way to the first reaction stage (WCR), while the catalyst is introduced around the tubes and the reaction takes place on the shell side of the GCR. In terms of their nominal width, the reaction stages are connected to large or very large pipelines; according to plant capacity, pipe diameters of up to 1 m are possible. This is particularly because of the large volumes of gas that are recycled to the second stage (recycle gas) and are mixed with the fresh gas, i.e. fresh synthesis gas from the gas production. The resulting gas mixture of recycle gas and fresh gas, after being preheated in the GCR, is fed to the first reaction stage (WCR). The volume of recycle gas is typically much greater than the amount of fresh gas and is dependent on the conversion achieved in the reactor section. The recycle ratio RR (RR=R/F) of recycle gas volume (R) to fresh gas volume (F) is often above 2 and in some cases is even above 3.5. The lower the conversion of synthesis gas through the reactor section per pass, the higher the recycle ratio RR required to achieve an adequate yield.

This correspondingly increases the circulating gas volume, which increases the stress on the reactors and requires greater nominal pipe widths of the connecting pipelines and also leads to a higher demand for compression energy (higher flow rate and pressure drop).

SUMMARY OF THE INVENTION

The problem addressed by the present invention is therefore that of specifying a reactor which does not have the described disadvantages of the reactors known from the prior art and which especially gives a high conversion based on the target products of the exothermic reaction per reactor pass and the option of readjusting and hence optimizing the reaction conditions along the longitudinal coordinate of the reactor, which in the case of the methanol synthesis, for example, leads to a reduction in the recycle ratio to smaller values as known in the case of use of the reactors known from the prior art.

This problem is solved by a reactor having the features of certain embodiments of the invention described herein.

Inventive Reactor:

Reactor for conducting exothermic equilibrium reactions, in which a gaseous feed mixture is at least partly converted over a solid catalyst to a product mixture comprising at least one liquid reaction product condensable at the reactor pressure and at temperatures below the reactor temperature, comprising at least two series-connected reaction cells that are in fluid connection with one another and are arranged in a common reactor shell, wherein each reaction cell comprises the following series-connected assemblies that are in fluid connection with one another:

(a) a preheating zone suitable for heating the feed mixture or the gaseous product stream from the upstream reaction cell, wherein the preheating zone can optionally be dispensed with in the first reaction cell in flow direction of the gaseous feed mixture, (b) at least one reaction zone comprising a catalyst active in respect of the exothermic equilibrium reaction to be conducted and a cooling apparatus in a heat-exchanging relationship with the catalyst, (c) at least one cooling zone comprising a cooling apparatus suitable for cooling the partly converted, gaseous product stream that has been laden with condensable reaction product and exits from the reaction zone to a temperature below the dew point of this gas, (d) a deposition zone comprising a phase separation apparatus for separation of the product stream that exits from the cooling zone into a gaseous product stream that has been freed of condensate and a condensate stream comprising liquid reaction product, (e) means of discharging the condensate stream comprising liquid reaction product and optionally means of feeding the condensate stream to a workup apparatus for the reaction product, (f) means of discharging the gaseous product stream that has been freed of condensate and means of feeding this gaseous product stream to a subsequent reaction cell arranged downstream and/or means of discharging the gaseous product stream from the reactor.

Fluid connection between two regions of the reactor of the invention is understood to mean any kind of connection that enables flow of a fluid, for example the feed gas stream or the synthesis gas product stream, from one to the other of the two regions, regardless of any intermediately connected regions or components.

What is meant by a heat-exchanging relationship is the possibility of heat exchange or heat transfer between two regions of the reactor according to the invention, wherein all mechanisms of heat exchange or heat transfer, such as conduction of heat, radiation of heat or convective heat transfer, may be manifested. An indirect heat-exchanging relationship is especially understood to mean the manner of heat exchange or of heat transfer through a wall (called passage of heat), which comprises the stages of heat transfer from fluid 1 to the surface of the wall, of conduction of heat through the wall and of heat transfer from the surface of the wall to fluid 2.

Means of introduction, discharge, etc. are understood to mean all the apparatuses, apparatus constituents, assemblies and components which enable the fluid in question to leave the spatial region in question, for example a vessel. This is especially understood to mean pipelines, pumps, compressors, other conveying devices and the corresponding passage orifices in the vessel wall.

The catalytic activity, especially in connection with a different catalytic activity on comparison of two different catalysts, is understood to mean the degree of conversion achieved per unit length of the catalyst bed from reactants to products. The activity is affected by the chemical composition, doping, poisoning, available surface area etc. of the catalyst material, but also by the geometry of the catalyst particles and textural parameters of the catalyst bed, for example the porosity or packing density thereof. Owing to the exothermicity of the reactions in question, a high catalytic activity correlates with a high release of heat per unit length of the catalyst bed.

The option mentioned in claim 1. (a) that the preheating zone in the first reaction cell in flow direction of the gaseous feed mixture can be dispensed with is implemented especially when a heating apparatus arranged outside the reactor according to the invention and connected upstream thereof is present, which assures the setting of the reaction temperature prior to entry into the first reaction zone.

The invention is based on the finding that an optimal temperature regime and repeated removal of products from the reaction zone can distinctly improve the production rates or space-time yields along the reaction pathway. The temperature profile along the reaction pathway is considerably improved by the use of a multistage reaction system, which achieves a distinctly higher conversion per pass.

By-product formation in the methanol synthesis is also reduced when the reactor according to the invention is used compared to the prior art.

An improved temperature profile in the reactor can in principle also be achieved with the aid of catalyst layer management. In this case, a less active catalyst would be used in the region in which the highest conversion (exothermicity) and hence the highest temperatures would be expected, and a more active catalyst in regions where less conversion is expected. However, such catalyst layer management is relatively inflexible since the various catalyst layers have to be selected and fixed on the basis of a particular catalyst activity and a corresponding gas composition. However, the catalyst activity changes as a result of its progressive deactivation over its onstream time in the synthesis plant.

The layer management and the corresponding cooling of the reaction bed have to be matched to one another. During the catalyst onstream time and the associated catalyst deactivation, the conditions change, and adjustment of the reaction temperature and the corresponding cooling/cooling temperature is desirable in order to at least partly compensate for the deactivation and to ensure a high conversion with low by-product formation. With the reactors known from the prior art, adjustment of the cooling can be undertaken for the entire reactor only; but not all catalyst layers are typically deactivated to the same degree over the operating time. The establishment of specific reaction conditions is therefore always a compromise.

By the approach according to the invention, the reaction conditions in the different reaction cells, by contrast, can also be adapted individually over the onstream time in each stage depending on the catalyst activity, the gas composition. In this way, a high conversion and low by-product formation are achieved in the various reaction cells.

With the optimized temperature regime, the maximum temperatures (and temperature peaks, called hotspots) in the catalyst bed are also reduced. As well as the discharge of the coproduct from the reaction system, for example of water in the methanol synthesis, this has a positive effect on the catalyst onstream time. It is known that both high temperatures in the catalyst bed and high water concentrations in the reaction gas lead to more rapid catalyst deactivation.

With the concept proposed, an improved space-time yield is achieved; it is thus also possible to considerably reduce the recycle gas volume (gas circulation). In principle, the reactor can thus be reduced in size and the pressure drop can also be reduced. Another result of the reduction in the recycle gas volume is that the amount and concentration of accumulated inert gases, for example unconverted methane from the synthesis gas production, in the synthesis gas circuit are distinctly reduced and hence the burden on the entire methanol synthesis cycle comprising reactor stages, circulation compressors and further equipment is reduced. The optimum can be considered to be the full conversion per reactor pass, where it would be possible to entirely dispense with a synthesis gas circuit and, therefore, no accumulation of inert gases occurs any longer. Such an approach is also of particular interest for other feed gas compositions with high inert gas components (for example a high proportion of nitrogen in synthesis gas production using air), since there is a rise in the volume of inert gas to be circulated in the synthesis gas circuit.

By controlled deposition of the liquid products and temperature control in the individual reaction cells, condensation in the catalyst bed is avoided and the catalyst is spared.

The condensates separated out with different proportions of methanol can be purified under different conditions or used directly as feed for downstream processes, which leads to an energy saving in the distillation.

In order to keep the apparatus complexity and the capital costs low, in accordance with the invention, multiple reaction stages or reaction cells and also multiple intermediate condensations and cooling and heating stages are implemented in one reactor. Connecting pipelines are avoided as far as possible, so as to reduce capital costs for pipelines and the pressure drop and to decrease the stress on the pipelines resulting from thermomechanical stresses. The process media are as far as possible guided from process stage to process stage within the apparatus.

In a preferred configuration of the reactor according to the invention, the cooling zone comprises the following in assembly (c):

(c1) a first cooling zone comprising a cooling apparatus suitable for cooling the partly converted, gaseous product stream that has been laden with condensable reaction product and exits from the reaction zone to a temperature below the temperature in the reaction zone, (c2) a second cooling zone comprising a cooling apparatus suitable for further cooling the partly converted, pre-cooled gaseous product stream that has been laden with condensable reaction product and exits from the first cooling zone to a temperature below the dew point of this gas.

By virtue of the configuration of assembly (c) with a first and a second cooling zone, there are more degrees of freedom with regard to the performance of the cooling of the partly converted, gaseous product stream that has been laden with condensable reaction product and exits from the reaction zone. For instance, in the first cooling zone, preliminary cooling can be effected, but without going below the dew point of the gas. The temperature is then lowered below the dew point for condensation in the second cooling zone. Alternatively, it is already possible for significant cooling with the temperature going below the dew point to be effected in the first cooling zone. In that case, the second cooling zone serves for further condensation of constituents that still remain in the gas phase but are condensable. Finally, it is possible to use different cooling media or else the same cooling medium at a different temperature level in the first and second cooling zones. This achieves improved thermal integration with regard to the reactor according to the invention or the process conducted therewith.

Heat carriers (heating media) or cooling media used are preferably media which are close to their boiling point and therefore readily evaporate (cooling medium) or condense (heat carrier). This assures good removal of heat by virtue of the good heat transfer on the part of the evaporating or condensing medium, and allows precise temperature regulation via the pressure. In order to establish different temperature conditions in the various stages, the pressure on the part of the heat carrier or cooling medium is regulated individually for each stage. With increasing catalyst onstream time, the conditions are adjusted by means of appropriate setting of the pressure on the cooling medium side and hence the reaction temperature is readjusted in order to keep the conversion correspondingly high.

With regard to the desired reaction conditions, water or steam can be used as heat carrier in the methanol synthesis. However, it is found that, when water is used, relatively large pressure differences have to be established for the desired temperature range, in order to cover a broad temperature range (e.g. 250° C. about 40 bar, 264° C. about 50 bar). If, by contrast, an evaporating heat carrier oil (e.g. Dowtherm A) is used in a circuit for steam generation, it is possible to work within a very tight pressure range and nevertheless to cover a wide temperature range (e.g. 255° C. 0.97 bar, 305° C. 2.60 bar, corresponding to a temperature range of 50° C. with a pressure difference of just 1.6 bar. In this way, it is possible to work with a simple heat carrier oil/steam drum at the corresponding plant level (about 20 to 25 m) and to make use of the geodetic feed height alone in order to establish the individual pressure or temperature ranges.

Cooling water or else an evaporating heat carrier can be used in the cooling zones and/or condensation zones, while a condensing or else liquid heat carrier can be used in the heating zones.

In a further preferred configuration of the reactor according to the invention, the shell is arranged horizontally or vertically with respect to the perpendicular imparted by gravity, wherein the flow of the gaseous feed mixture or the gaseous product stream from the upstream reaction cell through the reaction cells in both cases is vertical. This achieves advantages with regard to the arrangement of the catalyst in the reaction cell, since the flow of the gaseous feed mixture or the gaseous product stream from the upstream reaction cell through said catalyst is vertical and it can accordingly be in the form of a simple bed and merely has to be retained at its lower end by a support grid or similar devices.

In an alternative configuration of the reactor according to the invention, the shell is arranged horizontally or vertically with respect to the perpendicular imparted by gravity, wherein the flow of the gaseous feed mixture or the gaseous product stream from the upstream reaction cell through the reaction cells in both cases is horizontal. In this case, the fixing of the catalyst in the reaction cell is more complex, but advantages arise with regard to a catalyst exchange, which can then be undertaken in horizontal direction through inspection orifices provided for the purpose in the reactor shell, for example by suction.

In the case of a vertical arrangement of the shell, it is further preferable when the flow of the gaseous feed mixture or the gaseous product stream from the upstream reaction cell through the reaction cells is horizontal and in radial direction. Apart from the aforementioned advantages with regard to the catalyst exchange, further advantages arise in that longer pathways through the catalyst beds are enabled with equal or reduced pressure drop in the case of this arrangement.

It is particularly preferable when the preheating zone (a) and the first cooling zone (c1) coincide spatially or functionally and are in a heat-exchanging relationship with one another. In this case, the cooling medium heated or partly evaporated in the first cooling zone can be used simultaneously as heat carrier in the preheating zone, which achieves improved thermal integration with regard to the reactor according to the invention or the process conducted therewith.

In a further aspect of the reactor according to the invention, the reaction zone (b) is equipped with thermoplates, wherein the thermoplates consist of two sheets each bonded to one another, wherein this composite has, on its inside, a cavity which is tightly sealed from the outside and through which a fluid cooling medium or heat carrier flows, wherein the catalyst is present in the reaction zone in piece form or particulate form as a bed of solid material arranged between two adjacent thermoplates in each case in such a way that the gaseous feed mixture or the gaseous product stream from the upstream reaction cell can flow through it vertically or horizontally, and wherein the catalyst and the cooling medium are in an indirect heat-exchanging relationship. The thermoplates are notable in that they require a small amount of space with simultaneously good heat exchange properties. A further advantage is that they can simultaneously serve as holding or dividing devices for the catalyst bed.

In an alternative configuration, the preheating zone, the reaction zone or the cooling zones or more than one of these assemblies are executed as a lamellar heat exchanger. The advantages essentially correspond to those of the above-discussed configuration using thermoplates.

The cooling medium used is preferably hot condensate from a steam generator, wherein the cooling medium takes up at least a portion of the heat of reaction released in the reaction zone (b) and is partly evaporated, and wherein the condensate/saturated steam mixture obtained or the saturated steam is at least partly recycled to the steam generator and/or conducted as heat carrier to the preheating zone (a) of the same reaction cell. This medium can particularly effectively take up the heat of reaction which is released in the exothermic reaction that proceeds in the reaction zone, since the phase transition from liquid to vapour is associated with a particularly large change in enthalpy. Further advantages are associated therewith when the saturated steam formed is guided as heat carrier to the preheating zone of the same reaction cell. The enthalpy of evaporation is released particularly effectively here by condensation to the medium to be heated.

Further preferably, means are encompassed which permit at least partial recycling of the condensate/saturated steam mixture removed from one or more reaction cells or of the steam component only to the steam generator and at least partial release of the saturated steam drawn off from the steam generator as export steam to external consumers.

In a particular configuration of the reactor according to the invention, it comprises means which permit, in the preheating zone (a), the heating of the feed mixture or of the gaseous product stream from the upstream reaction cell in indirect heat exchange against hot condensate from a steam generator, to obtain a cooled hot condensate stream. Means of the type mentioned may be pipelines, closed-loop control units such as valves, and other devices suitable for this purpose.

In a further particular configuration of the reactor according to the invention, it comprises means which permit supply of the cooled hot condensate stream from the first cooling zone (c1), removed from the preheating zone (a), as cooling medium in a preceding reaction cell arranged upstream, followed by recycling thereof to the steam generator. In this way, the thermal integration within the reactor according to the invention is improved and the input and output streams to and from the steam generator are reduced.

Preferably, in the reactor according to the invention, at least some of the cooling zones and/or preheating zones are configured as plate heat exchangers with thermoplates. The thermoplates are notable in that they require a small amount of space with simultaneously good heat exchange properties. When the reaction zones are also equipped with thermoplates, further advantages arise with regard to a more consistent reactor construction and logistical advantages for the stockholding of replacement parts.

In a further aspect of the reactor according to the invention, it comprises means which permit supply of fresh feed mixture that has not yet been partly converted to one or more of the subsequent reaction cells arranged downstream of the first reaction cell. Alternatively or additionally, it is also possible to supply individual reactants, for example CO, $CO_2$ or $H_2$ in the case of methanol synthesis, in order to have a favourable effect on the kinetics or equilibrium position of the reaction. Means of the type mentioned may be pipelines, closed-loop control units such as valves, and other devices suitable for this purpose. It is advantageous here that the higher chemical reaction potential of the freshly supplied feed mixture substream that has not yet been preconverted is utilized, and so the equilibrium reaction is shifted in the direction of the target products.

In a further particular configuration of the reactor according to the invention, the reaction zone (b) is equipped, in at least one reaction cell, with at least two catalysts having different activity with regard to the exothermic equilibrium reaction. The catalytic activity of the first catalyst layer arranged upstream may, for example, be higher than the catalytic activity of the second catalyst layer arranged downstream, the activity being understood to mean the degree of conversion in the catalyst per unit length of the catalyst bed.

The provision of a first, upstream layer of catalyst material with higher catalytic activity achieves a high conversion of synthesis gas at the start of the catalyst bed and release of a correspondingly large amount of heat. This achieves a temperature of around 250° C. which is optimal for the reaction. The further catalyst layer with lower catalytic activity prevents or reduces the formation of a pronounced hotspot that could rapidly worsen the catalyst activity. A developing hotspot, with increasing operating time, is at first sharp and high, becomes increasingly broader and flatter and additionally migrates downstream.

Advantageously, the layer thickness of the first, upstream catalyst layer is chosen to be much smaller than the layer thickness of the downstream layer. In this case, the upstream, highly active catalyst layer serves to heat up the catalyst bed to an optimal temperature. Further down the catalyst bed, i.e. in the region of the second, downstream catalyst layer with lower activity, less heat is released and deactivation of the catalyst is prevented. The layer thickness of the first catalyst layer is chosen such that no temperature that would enable the development of a pronounced hotspot is attained within this thin layer.

A further possible configuration results from use of different forms of catalyst in different reaction zones and/or in different catalyst layers. This improves the efficiency per catalyst pellet and the conversion is additionally increased as a result.

The invention also relates to the use of a reactor according to one of the configurations described above for preparation of methanol by conversion of a synthesis gas feed comprising hydrogen and carbon oxides, especially carbon dioxide. It is particularly favourable here that the methanol reaction product can be condensed out in the individual reaction cells by technically simple measures.

BRIEF DESCRIPTION OF THE DRAWINGS

Developments, advantages and possible uses of the invention will also be apparent from the description of working examples which follows and the drawings. The invention is formed by all the features described and/or shown in figures, alone or in any combination, irrespective of their assembly in the claims or the dependency references thereof.

The figures show.

DETAILED DESCRIPTION OF THE INVENTION

Figure 1:
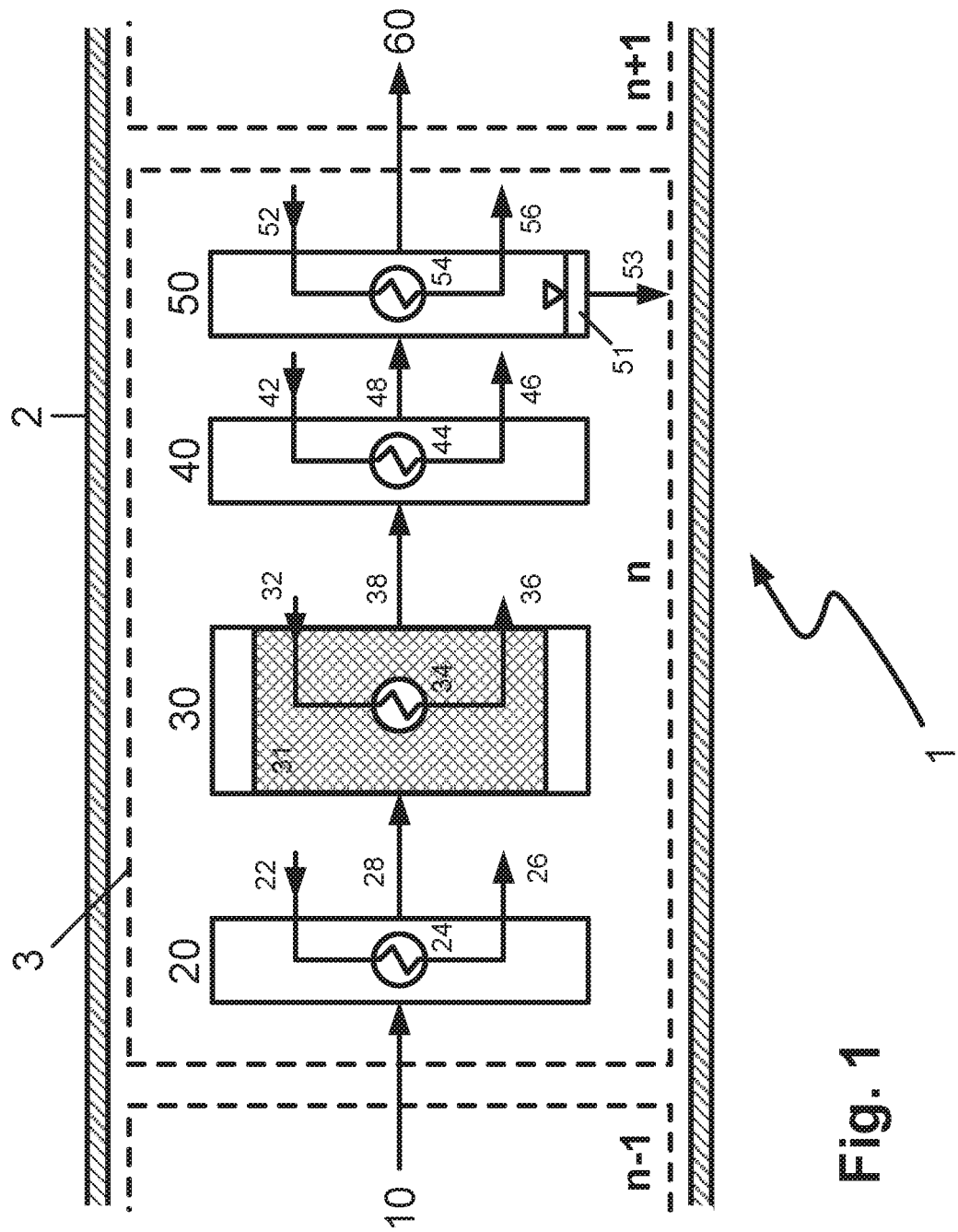
FIG. 1 a reaction cell in a reactor in a first embodiment of the invention.

FIG. 1 is a schematic diagram of a reaction cell 3 in a reactor 1 in a first embodiment of the invention. The reaction cell n is within the reactor shell 2, the inner wall of which forms the outward physical boundary of the reactor and bears the pressure chosen for the performance of the exothermic equilibrium reaction.

Via conduit 10, the preheating zone 20 is supplied, in the reaction cell n, with the gaseous, pre-reacted product stream from the preceding reaction cell n−1 arranged upstream. If the reaction cell n is the first reaction cell in flow direction, the feed mixture is fed in via conduit 10.

In the preheating zone 20, the gaseous product stream or the feed mixture is heated up to the reaction temperature. This is effected in indirect heat exchange against a heating fluid which is fed via conduit 22 to the heat exchanger 24, where it transfers its heat content to the gaseous product stream or the feed mixture. The cooled heating fluid is removed from the heat exchanger via conduit 26 and heated up in a heating apparatus which is not shown in the figure, in order to feed it back to the heat exchanger 24.

The heated feed mixture or the heated gaseous product stream is fed via conduit 28 to the reaction zone 30 which contains a bed of a catalyst 31 active in respect of the exothermic equilibrium reaction to be performed and a cooling apparatus 34 in a heat-exchanging relationship with the catalyst. The heat of reaction released by the exothermic reaction is removed in indirect heat exchange against a cooling fluid, optionally in partly evaporated form, which is fed via conduit 32 to the heat exchanger 34 and, after absorbing the heat of reaction released in the catalyst bed, is removed via conduit 36. The heated cooling fluid is cooled down again in a cooling apparatus which is not shown in the figure, in order to feed it back to the heat exchanger 34.

In the reaction zone, under the reaction conditions chosen, the feed mixture or the gaseous product stream from the reaction cell n−1 is partly converted in the catalyst bed to a gaseous product stream laden with condensable reaction product, which is removed from the reaction zone via conduit 38 and fed to a first cooling zone 40.

In the first cooling zone 40, the gaseous product stream laden with condensable reaction product is subjected to preliminary cooling, wherein the first proportions of condensate can already be obtained, which can be discharged from the reactor 1 via a deposition apparatus, not shown in the figure, and conduits. Alternatively, the preliminary cooling can also be conducted in the first cooling zone in such a way that the temperature does not yet go below the dew point of the gas stream. The preliminary cooling is effected in indirect heat exchange against a cooling fluid which is fed via conduit 42 to the heat exchanger 44 and, after absorbing heat, removed via conduit 46. The heated cooling fluid is cooled again in a cooling apparatus, not shown in the figure, in order to feed it back to the heat exchanger 44.

The gaseous product stream that has been precooled but is still laden with at least a portion of the condensable reaction product is discharged from the first cooling zone via conduit 48 and fed to the second cooling zone 50. In the second cooling zone 50, the gaseous product stream laden with condensable reaction product is cooled further, going below its dew point. This affords a liquid condensate which is separated from the gas stream by means of a deposition apparatus 51 integrated into the second cooling zone and discharged from the reactor by means of conduit 53 and fed to the product workup system which is not shown in the figure. The cooling is effected in indirect heat exchange against a cooling fluid which is fed via conduit 52 to the heat exchanger 54 and, after absorbing heat, removed via conduit 56. The heated cooling fluid is cooled down again in a cooling apparatus not shown in the figure, in order to feed it back to the heat exchanger 54.

The gaseous product stream that has been cooled and freed of condensate is discharged via conduit 60 from the second cooling zone 50 and hence also from the reaction cell n. It is then fed to the downstream reaction cell n+1 in order to enable further conversion of the gaseous reactants to target products. If no further conversion of the gaseous reactants is desirable or possible, the remaining tail gas is discharged from the reactor via conduit 60 and sent for further workup or disposal. Alternatively, the tail gas stream can be applied to the reactor again after recycling and mixing with fresh feed mixture.

In the configurations of the inventive reactor shown in schematic form in FIG. 2 to FIG. 7, identical reference numerals correspond in principle to the apparatus constituents as already described in the elucidation of the first configuration of the invention, FIG. 1. The respective operating steps and process conditions are also the same, unless described differently hereinafter.

Figure 2:
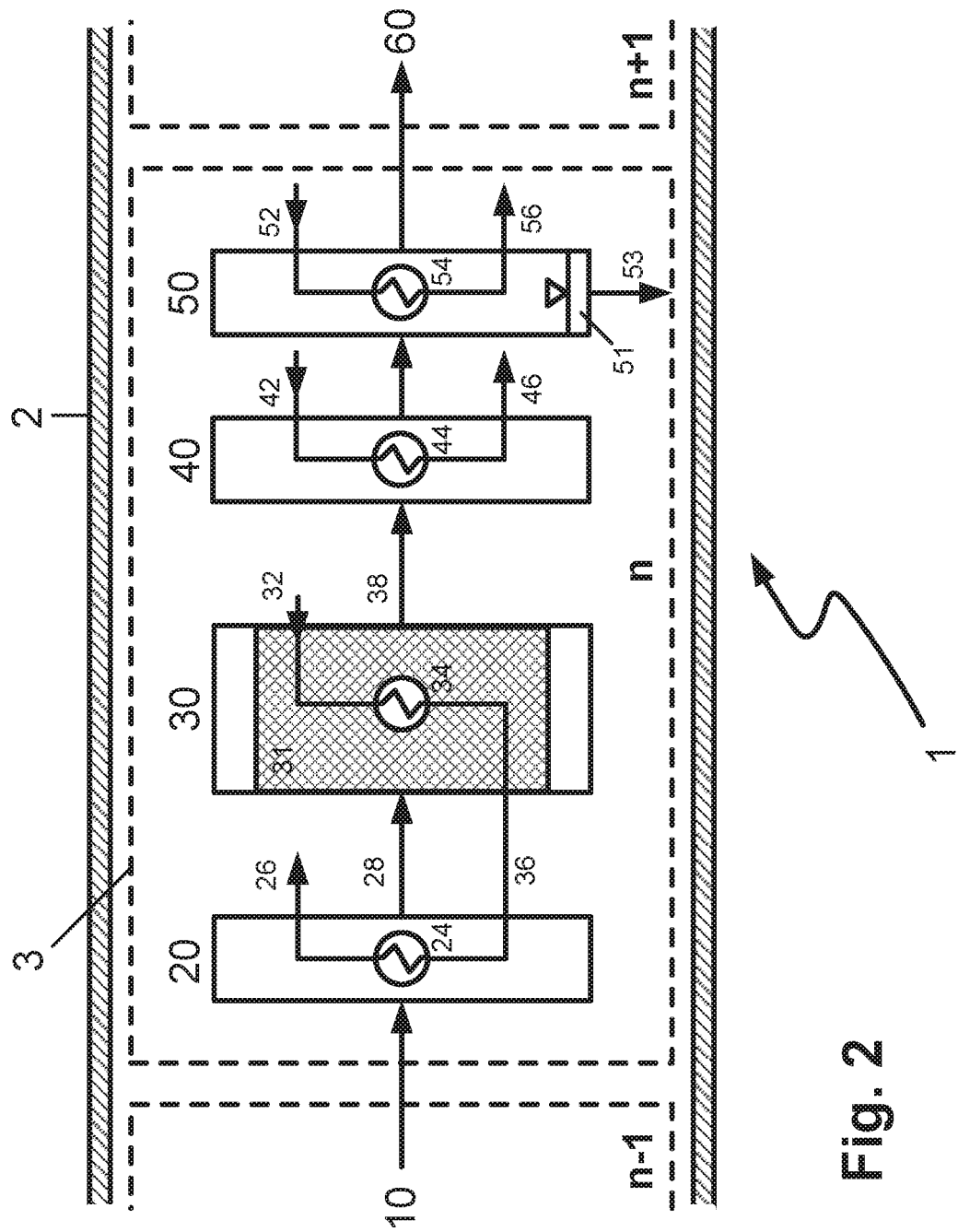
FIG. 2 a reaction cell in a reactor in a second embodiment of the invention, FIG. 3 a reaction cell in a reactor in a third embodiment of the invention, FIG. 4 a reaction cell in a reactor in a fourth embodiment of the invention, FIG. 5 a first example of the connection of two successive reaction cells in a reactor according to the invention, FIG. 6 a second example of the connection of two successive reaction cells in a reactor according to the invention, FIG. 7 a working example for the connection of a reaction cell in a reactor according to the invention having a steam generator.

By contrast with the first configuration, in FIG. 2, the cooling fluid heated up by absorption of the heat of reaction in the reaction zone 30 is conducted via conduit 36 to the heat exchanger 24 of the preheating zone 20, where it is used as heating fluid for the heating of the feed mixture or the gaseous product stream from the upstream reaction cell. In this way, thermal integration within the reactor is improved. This option is of particular interest when a (partly) evaporating cooling medium is used in the reaction zone 30 and is at least partly condensed again in the preheating zone 20, where it is used as heating medium. In the case of a vertical arrangement of preheating zone (at the top) with a reaction zone beneath, this can be achieved in a simple manner with a single arrangement comprising an upper preheating zone without catalyst and a lower reaction zone comprising catalyst, which are directly connected on the heat exchanger side. Steam formed from the reaction zone ascends and is used at least partly as heating medium in the preheating zone; condensed steam flows back to the reaction zone in liquid form. The heating fluid cooled down by heat exchange with the gas stream supplied in conduit 10 can subsequently, optionally after further cooling in a cooling apparatus not shown in the figure, be recycled as cooling fluid via conduit 32 to the heat exchanger 34 of the reaction zone 30.

Figure 3:
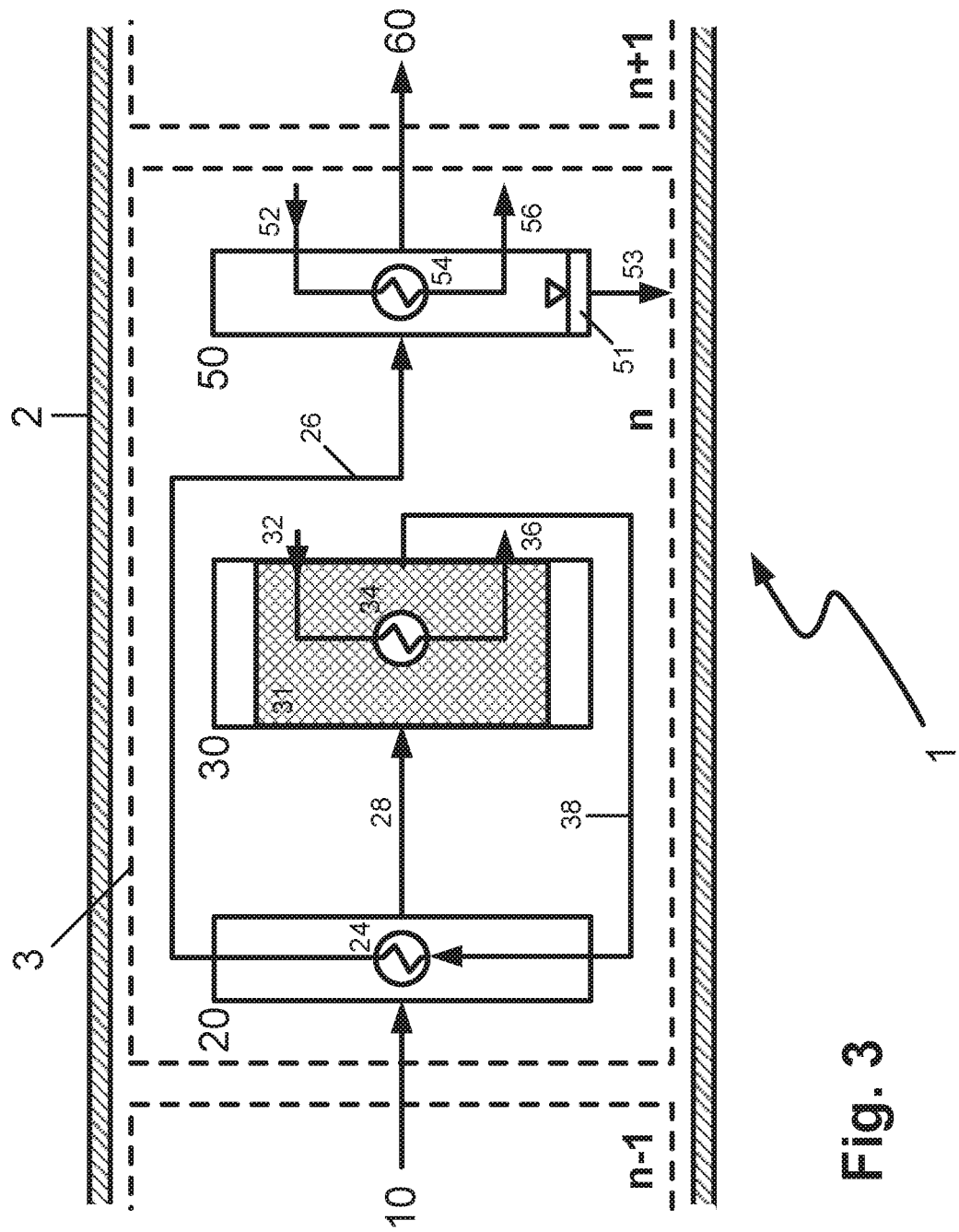

By contrast with the first configuration, in FIG. 3, the product stream discharged from the reaction zone 30 via conduit 38 is guided as heating fluid to the heat exchanger 24 of the preheating zone 20, where it serves to heat up the feed mixture or gaseous product stream brought in via conduit 10 from the upstream reaction cell. The preheating zone 20 and the first cooling zone 40 thus coincide. In this way too, thermal integration within the reactor is improved. The product stream cooled by heat exchange is then guided via conduit 26 to the second cooling zone 50.

Figure 4:
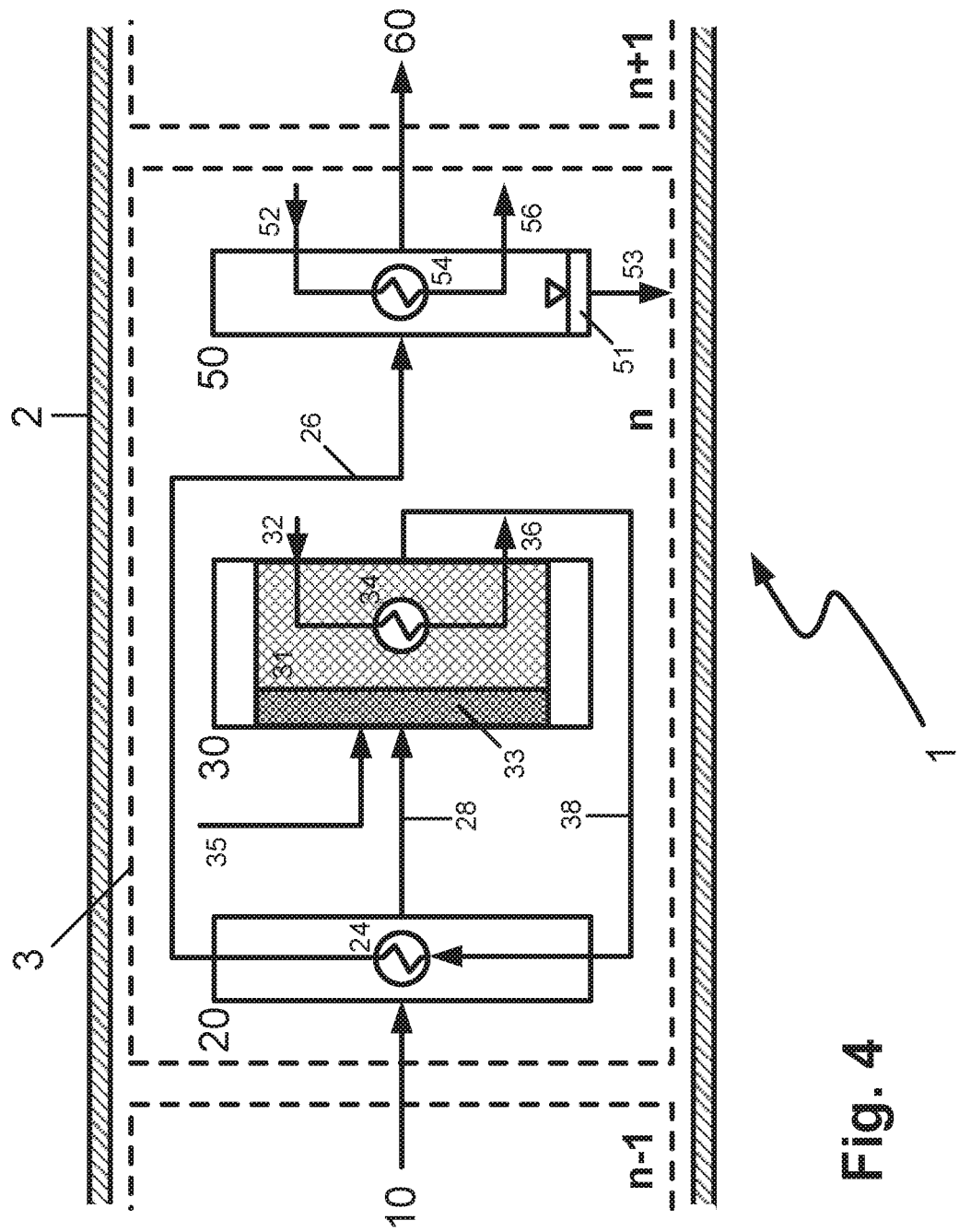

By contrast with the above-elucidated configuration according to FIG. 3, the reaction zone in FIG. 4 contains two beds of catalysts 31, 33 having different activity in respect of the exothermic equilibrium reaction, through which the feed mixture or gaseous product stream from the upstream reaction cell flows successively. In the configuration shown, only the downstream catalyst bed 31 is cooled by means of the cooling apparatus 34. One possible configuration envisages that the catalyst bed 33 contains a catalyst having a higher activity compared to the catalyst bed 31. In this way, the catalytic conversion can first be set in motion and the amount of heat released contributes to the heating of the reaction mixture to the chosen inlet temperature into the catalyst bed 31, which means that the heat exchanger 24 in the preheating zone 20 can be reduced in size. For this function as ignition catalyst, experience has shown that a small or short catalyst bed in relation to the main catalyst bed 31 is sufficient. The reaction in the main catalyst bed 31 then proceeds more homogeneously, since spikes in concentration of the reactants are already reduced in the catalyst bed 33 and, in addition, the catalyst bed 31 is cooled. This avoids the formation of hotspots.

Alternatively, it is possible to use a catalyst having lower activity compared to the catalyst bed 31 in the catalyst bed 33. This is advisable particularly when the reaction potential of the gas mixture that occurs in the reaction zone is high. This is the case in the configuration shown in FIG. 4 since, via conduit 35, the reaction zone 30 is supplied in the reaction cell n with fresh, i.e. as yet non-prereacted feed mixture or individual reactants. In this way, the reaction is set in motion in a slower and more controlled manner and the majority of the heat of reaction is released in the cooled catalyst bed 31.

The feeding of fresh, as yet non-prereacted feed mixture or individual reactants to reaction cells with n>1 may also be viable in conjunction with the other configurations of the reactor according to the invention that have been discussed here. In addition, it may be advantageous to feed fresh, as yet non-prereacted feed mixture to more than one reaction cell with n>1.

Figure 5:
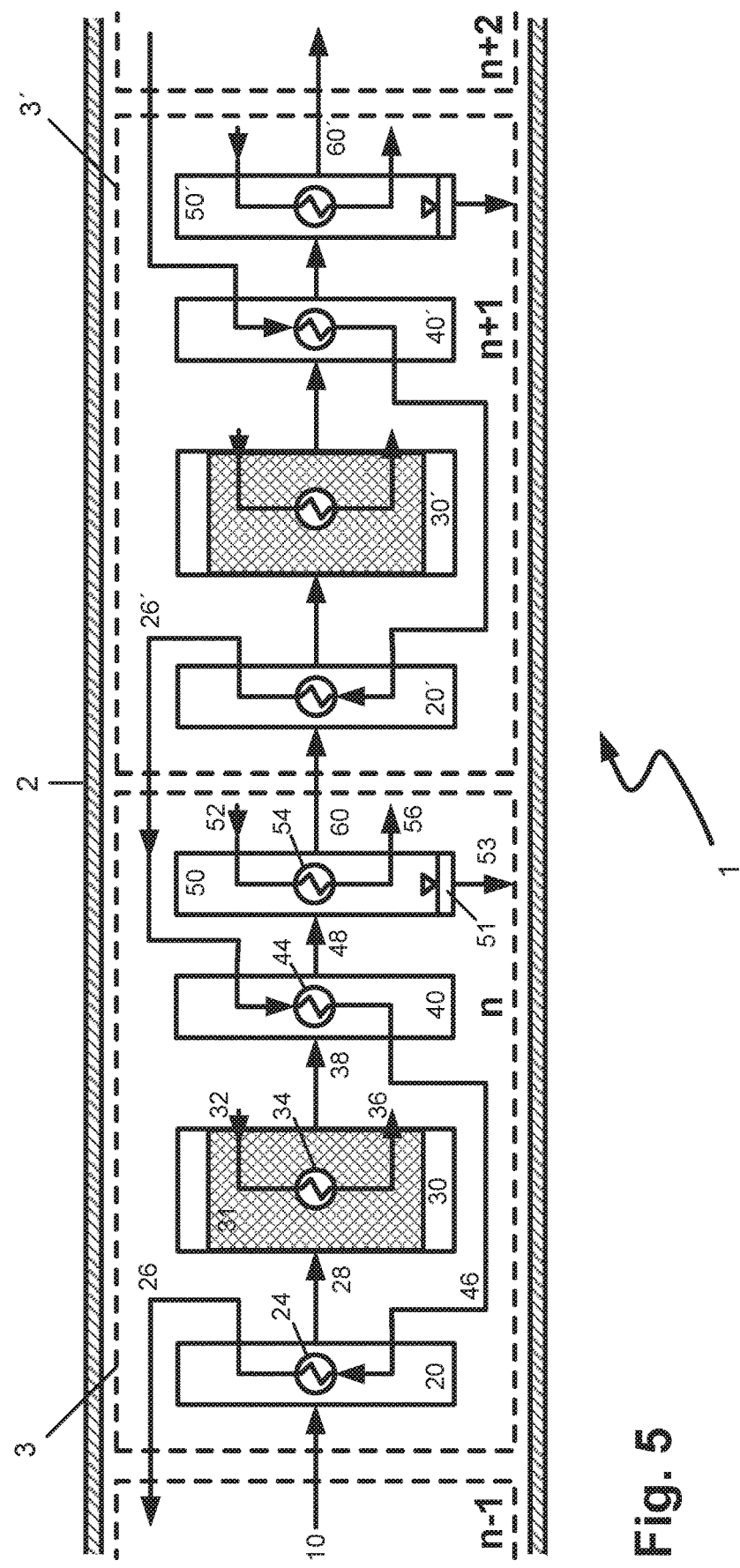

The configuration of the reactor according to the invention shown in schematic form in FIG. 5 shows one possible connection of two successive reaction cells n and n+1. Corresponding apparatus constituents of the reaction cell n+1 are identified by an apostrophe ' after the respective reference numeral. In this case, cooled heating fluid from the preheating zone 20' of the reaction cell n+1 is fed via conduit 26' to the heat exchanger 44 in the first cooling zone 40 of the reaction cell n, where it serves to precool the gas stream removed from the reaction zone 30 via conduit 38. Correspondingly, cooled heating fluid from the preheating zone 20 from the reaction cell n is fed via conduit 26 to the corresponding heat exchanger in the first cooling zone of the reaction cell n−1. In this way, even further thermal integration within the reactor is achieved, which now extends over multiple reaction cells. The heating fluid heated up in the heat exchanger 44 is fed via conduit 46 to the heat exchanger 24, where it serves to preheat the mixture entering the reaction cell n via conduit 10.

Figure 6:
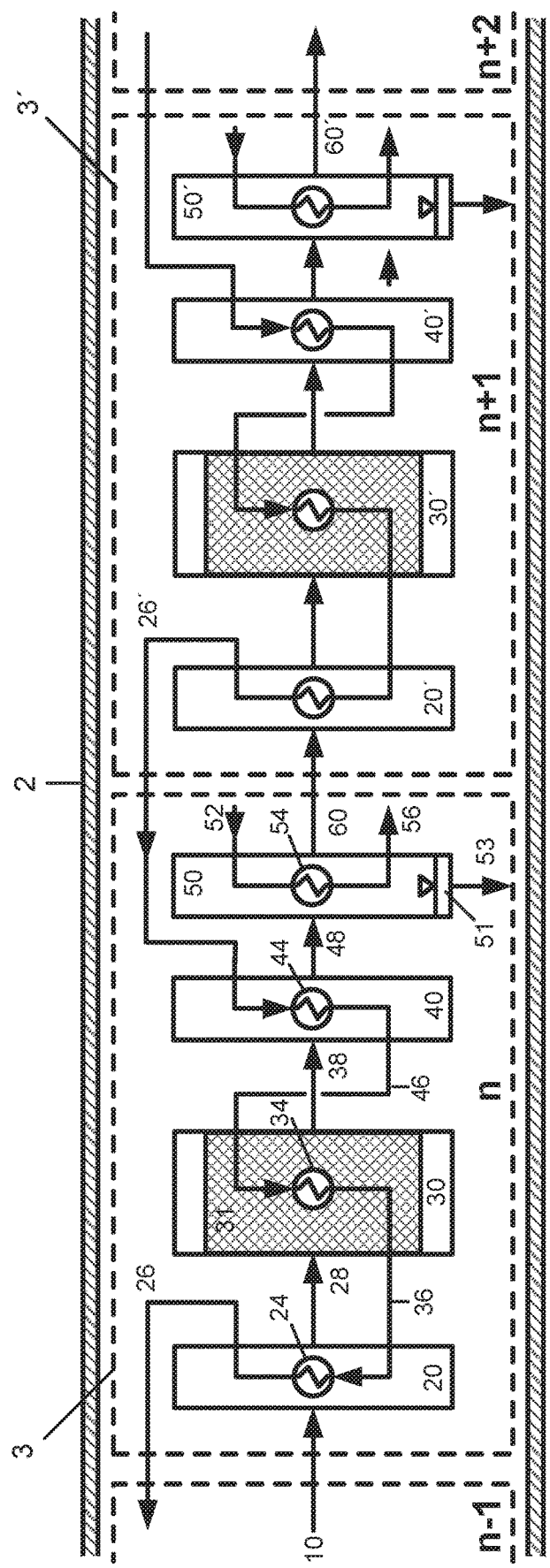

By contrast with the above-discussed configuration according to FIG. 5, in the working example of FIG. 6, in addition, the heated coolant removed from the respective first cooling zone 40, 40' etc. is fed to the heat exchanger of the respective upstream reaction zone 30, 30' etc. as coolant. The coolant which is heated further in the reaction zone is subsequently fed to the heat exchanger of the respective upstream preheating zone as heating fluid. This configuration may especially be suitable for conducting moderately exothermic reactions. It is still favourable in the context of this configuration to use a cooling fluid/heating fluid having high heat absorption and heat release capacity; suitable fluids for this purpose are especially those which, when used as cooling fluid or heating fluid, have a liquid-vaporous phase transition or vice versa. Finally, it can be advisable to cool the reaction zones by means of further cooling apparatuses not shown in the figure in order to have a more intense cooling effect and more degrees of freedom with regard to the temperature regime in the reaction zone.

In the last two configurations of the reactor according to the invention discussed, it may additionally be advisable to feed the heated cooling fluids or cooled heating fluids first to one or more cooling or heating apparatuses arranged outside the reactor, in order to restore the full heat absorption or heat release capacity of the respective fluid. These external cooling or heating apparatuses could be arranged, for example, within the flow pathway of the conduits 26, 26' etc. (heating), 46, 46' etc. (cooling) or 36, 36' etc. (cooling).

Figure 7:
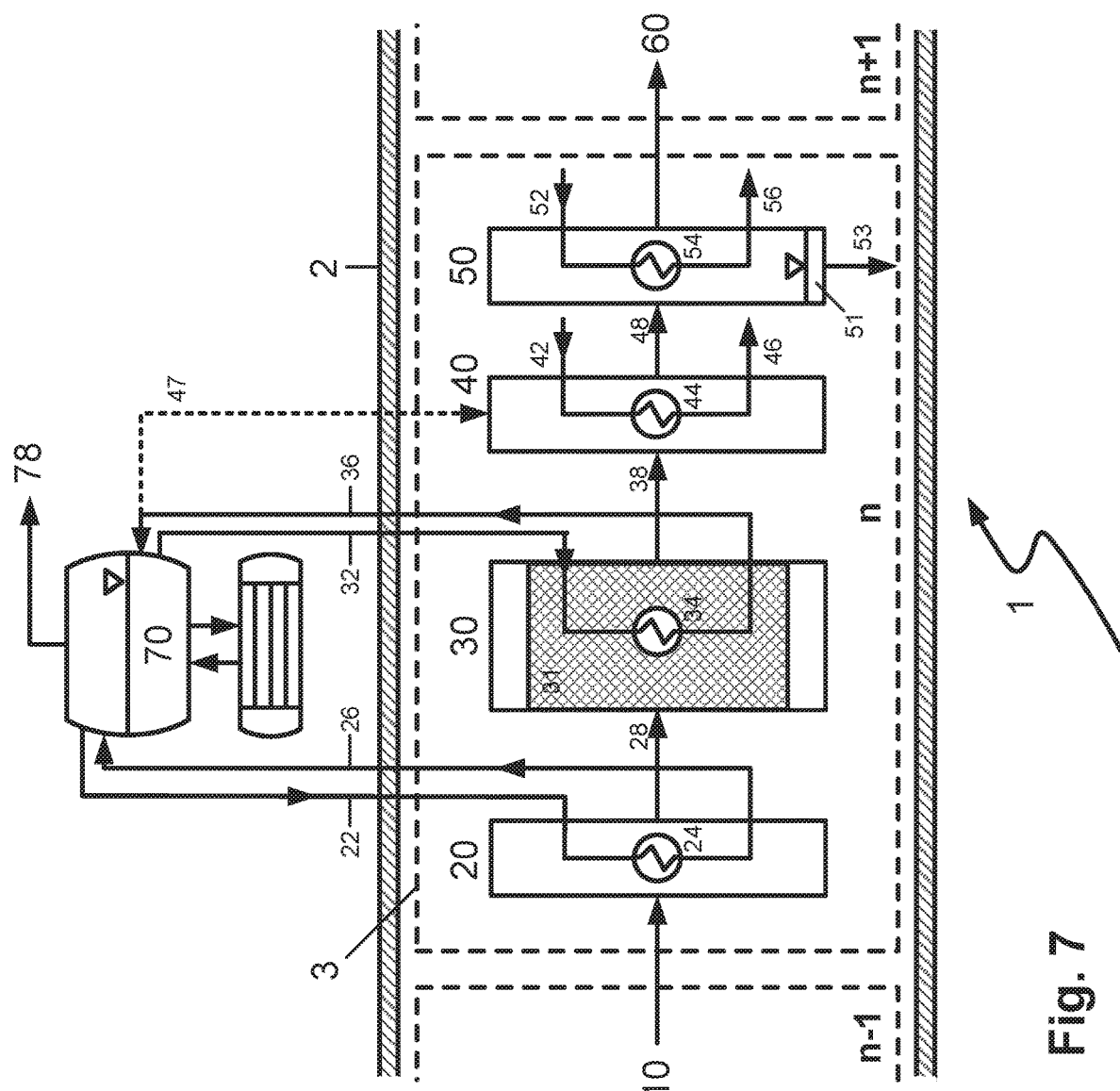

The connection with an external cooling or heating apparatus is shown in schematic form in the configuration shown in FIG. 7, in which a steam generator 70 is arranged outside the reactor. Hot condensate is withdrawn therefrom and fed as coolant via conduit 32 to the heat exchanger 34 of the reaction zone 30, where it is partly evaporated. The resulting biphasic mixture in liquid/vaporous form is recycled to the steam generator via conduit 36.

The hot condensate from the steam generator 70 can also be used as coolant in the first cooling zone 40; this is shown in schematic form by the dotted conduit 47.

Also withdrawn from the steam generator 70 is saturated steam, which is fed via conduit 22 to the heat exchanger 24 of the preheating zone 20. The release of heat to the stream brought in via conduit 10 results at least in partial condensation. The resulting stream can either be recycled directly via conduit 26 to the steam generator or can be collected by means of other apparatuses (not shown in the figure) and then at least partly recycled back to the steam generator, in order to be evaporated again there.

In the working example of FIG. 7, moreover, saturated steam can be removed from the steam generator 70 via a conduit 78 and released as export steam to external consumers.

The heat carriers or cooling media used are preferably media that are close to their boiling point and therefore readily evaporate (cooling medium) or condense (heat carrier, heating medium). This assures good removal of heat by virtue of good heat transfer on the part of the evaporating or condensing medium, and allows precise regulation of temperature via the pressure. In order to establish different temperature conditions in the various stages, the pressure is regulated individually for each stage on the part of the heat carrier or cooling medium. With increasing catalyst onstream time, the conditions are adjusted by means of appropriate setting of the pressure on the cooling medium side, and hence the reaction temperature is readjusted in order to keep the conversion correspondingly high.

With regard to the reaction conditions desired, it is possible for example to use steam as heat carrier in methanol synthesis. However, it is found that, when water is used, relatively large pressure differences have to be established for the desired temperature range in order to cover a broad temperature range (e.g. 250° C. about 40 bar, 264° C. about 50 bar). If, by contrast, an evaporating heat carrier oil (e.g. Dowtherm A) is used in a circuit for steam generation, it is possible to work within a very narrow pressure range and nevertheless to cover a large temperature range (e.g. 255° C. 0.97 bar, 305° C. 2.60 bar, corresponding to a temperature range of 50° C. with a pressure differential of just 1.6 bar. In this way, it is possible to work with a simple heat carrier oil/steam drum at the appropriate plant level (about 20 to 25 m), and to make use of the difference in height alone in order to establish the individual pressure or temperature ranges.

Cooling water or else an evaporating heat carrier can be used in the cooling zones and/or condensation zones, while a condensing or else liquid heat carrier can be used in the heating zones.

In many configurations of the reactor according to the invention, for example in all the configurations discussed above, it may be advantageous to form each of the heat transport spaces by means of at least one thermoplate. The heat transport spaces are understood to mean the regions of the reactor in which there is heat exchange between the gas flow containing the reactants or reaction products and heating or cooling fluids, i.e. the preheating zone, the reaction zone and the cooling zones.

A thermoplate in the context of the invention consists of two sheets which are bonded, preferably welded together, at the edges, and which have a multitude of additional bonds, preferably point welds, which likewise connect the plates to one another, distributed over the surface thereof. Plates of this kind can be manufactured in an automated manner by robots or machines and hence at very favourable cost. After the welding, the sheets are expanded by hydraulic forming, generally the injecting of a liquid under high pressure, which gives rise to cushion-shaped channels between the sheets, through which a heating or cooling fluid can be passed. By means of the heat transport spaces, therefore, heat energy can be either supplied to or removed from particular regions of the reactor through the passage of heating or cooling fluids.

When thermoplates are used, the reaction zones can be configured such that two thermoplates are first arranged essentially parallel in the reactor. "Essentially parallel" in the context of the invention means that the relative alignment of the thermoplates differs from parallel by a maximum of +/−20°, preferably by a maximum of +/−10°, more preferably by a maximum of +/−5°, most preferably by a maximum of +/−2°. Accordingly, the clear space between the thermoplates can be filled up with a bed of a solid, granular, particulate or pelletized catalyst, in which case the lateral closure of the resulting catalyst bed is formed by meshes, grids, perforated plates, grilles, beds of inert material and/or the inner reactor wall.

More preferably, this arrangement is adjoined by at least one, preferably more than one, further thermoplate spaced apart in a parallel arrangement, resulting overall in an assembly of plates, where the clear spaces between the thermoplates are filled up with catalyst beds. In this way, a compact, sandwich-like structure with an intensive cooling apparatus that extends over the length of the reaction zone is obtained in the reaction zone. The individual catalyst beds are charged here with the reaction gas mixture in parallel. The plate assemblies can, based on the clear spaces filled with catalyst, be aligned in parallel or at right angles to the longitudinal axis of the reactor.

The distances between the thermoplates are selected according to the exothermicity of the reaction to be conducted: for highly exothermic reactions, the distance chosen is smaller than for more weakly exothermic reactions. In this case, preference is given to smaller plate distances in the first reaction zone, since the greatest conversion is achieved here and the greatest removal of heat has to be implemented. The thermoplate distances in the first reaction zone, in the case of methanol synthesis, are preferably 20 to 45 mm. The distance is based on the distance from centre line to centre line, meaning that the clear distance between the plates, according to the thermoplate thickness and expansion of the cavity, is correspondingly smaller. Moreover, the distance is matched to the dimensions of the catalyst particles in order to assure optimal removal of heat and good bulk material characteristics in the filling and emptying of the catalyst without bridge formation. In the second and subsequent reaction zones, the distances chosen are typically greater.

Especially in the case of horizontal arrangement of the reactor with simultaneously vertical arrangement of the catalyst beds in the reaction zones, there is the possibility of simple removal of the catalyst from the reactor for the purpose of catalyst exchange. In this case, for emptying, appropriate inspection orifices should be provided in the reactor shell, which are actuated, for example, by means of a flap or slide mechanism. The slide mechanism can be executed in a very space-saving manner; it is advantageous here when the support grilles of the adjacent reaction zones can be moved one over the other by means of appropriate guide rails, such that adjacent regions can be emptied successively.

In a particular configuration, adiabatic, i.e. uncooled, reactor beds can be provided both downstream and upstream of the cooled plate assemblies. This may be of interest particularly when just a residual conversion is still to be achieved and cooling of the reaction is no longer necessary owing to the small evolution of heat, or on entry into a reaction stage where it is advantageous to achieve a rapid increase in temperature before the reactants enter the cooled region of the reaction zone.

In the case of the configuration of the preheating zone and cooling zones too, thermoplates can advantageously be used in the manner of a plate heat exchanger. It is possible here to dispense with the use of tube end plates as required in the case of shell-and-tube heat exchangers. Moreover, logistical and manufacturing advantages are obtained, since there is a reduction in the number of different components of the reactor and hence in the complexity of the apparatus. A further possible configuration of the reactor according to the invention is enabled by the configuration of the heat transport spaces by means of lamellar heat exchangers (plate-fin heat exchanger) alternatively or additionally to the use of thermoplates.

Numerical Examples

Comparison of the Reactor According to the Invention with Reactors Known from the Prior Art In the tables which follow, characteristic data of the reactor according to the invention are compared with reactors known from the prior art for the heterogeneously catalysed synthesis of methanol from synthesis gas.

In the first comparison case, a reactor according to the invention having three reaction cells is compared with a three-stage industrial reactor comprising two water-cooled reactors WCR connected in parallel, followed downstream by a gas-cooled reactor GCR. The industrial plant does not have any intermediate condensation between WCR and GCR. The feed gas is the same in both cases in terms of its composition and flow rate; this is a synthesis gas having the following composition: 8.4% by volume of $CO_2$, 20.1% by volume of CO, 68% by volume of $H_2$, the remainder being inert components. The inlet pressure into the reactor in each case is 75 bar gauge. In Table 1, the essential comparative data for the two reactors are correlated. In the table, $X_{pp}(k)$ means the conversion of component k per pass through the reactor and $X_{tot}(k)$ the total conversion thereof over the reactor including gas circulation. STY is the space-time yield of methanol in kg/h, based on one litre of catalyst volume.

TABLE 1

Comparison of the characteristic data of the reactor according to the invention having three reaction cells with a three-stage methanol synthesis reactor (2 parallel WCRs + GCR) according to prior art.

|  | Methanol synthesis reactor with 2 parallel WCRs + GCR Comparative Example | Inventive reactor (three reaction cells) |
|---|---|---|
| $X_{pp}(CO)/\%$ | 81.9 | 95.5 |
| $X_{pp}(CO_2)/\%$ | 28.0 | 60.7 |
| $X_{pp}(CO_x)/\%$ | 54.6 | 82.7 |
| $X_{tot}(CO)/\%$ | 99.2 | 99.1 |
| $X_{tot}(CO_2)/\%$ | 85.4 | 84.4 |
| $X_{tot}(CO_x)/\%$ | 95.2 | 94.4 |
| STY(MeOH)/kg/(h litre$_{cat}$) | 0.86 | 1.26 |
| $V_{cat, tot}/m^3$ | 315 | 180 |
| $T_{in}/°C.$ | 230 | 215 |
| $T_{max}/°C.$ | 270 | 230 |
| By-products/ppm | 6200 | 3250 |
| Recycle ratio | 2.2 | 0.5 |

As apparent from the data collated in Table 1, the conversion of carbon oxides for the overall reactor is comparable in both cases; however, the conversions per reactor pass are much higher for the reactor according to the invention. For the latter, moreover, the maximum temperature in the catalyst bed, the concentration of by-products and the recycle ratio required are lower.

Table 2 below compares a one-stage, water-cooled reactor for methanol synthesis with a reactor according to the invention comprising four reaction cells, the reactor according to the invention being operated without recycling. The feed gas is the same in both cases with regard to composition and flow rate; this is a synthesis gas having the following composition: 7% by volume of $CO_2$, 16% by volume of CO, 73% by volume of $H_2$, the remainder being inert components. The inlet pressure into each of the reactors is 75 bar gauge.

TABLE 2

Comparison of the characteristic data of the reactor according to the invention having four reaction cells without recycling with a one-stage water-cooled methanol synthesis reactor

|  | Methanol synthesis reactor (one-stage cooled reactor with high gas recycling rate) Comparative Example | Reactor according to the invention (four reaction cells without gas recycling) |
|---|---|---|
| $X_{pp}(CO)/\%$ | 90.8 | 99.7 |
| $X_{pp}(CO_2)/\%$ | 62.8 | 93.9 |
| $X_{pp}(CO_x)/\%$ | 80.6 | 97.8 |
| $X_{tot}(CO)/\%$ | 99.2 | 99.7 |
| $X_{tot}(CO_2)/\%$ | 94.7 | 93.9 |
| $X_{tot}(CO_x)/\%$ | 97.9 | 97.8 |
| STY(MeOH)/kg/(h litre$_{cat}$) | 0.98 | 1.15 |
| Recycle ratio | 3.5 | 0 |

The reactor according to the invention with four reaction cells achieves a higher space-time yield of methanol by around 15% without recycling. More particularly, the $CO_2$ conversion per reactor pass is much higher than in the comparative example.

Optimization of the Process Conditions in the Reactor According to the Invention The tables which follow indicate the effect of particular process parameters in the individual reaction cells of the reactor according to the invention in the heterogeneously catalytic synthesis of methanol from synthesis gas. The other process conditions correspond to those from the example shown in Table 2 (referred to as Reference in Tables 3 to 5).

TABLE 3

Variation in the distribution of the catalyst volume

| | $V_{cat}/m^3$ | | | | | $X_{tot}(CO_x)/$ | STY(MeOH)/ kg/(h |
|---|---|---|---|---|---|---|---|
| Case | 1st stage | 2nd stage | 3rd stage | 4th stage | total | % total | $l_{cat}$) total |
| Reference | 8 | 8 | 8 | 8 | 32 | 95.1 | 1.53 |
| 1 | 4 | 6 | 10 | 12 | 32 | 92.1 | 1.49 |
| 2 | 12 | 10 | 6 | 4 | 32 | 96 | 1.56 |

TABLE 4

Variation in the cooling temperature $T_{cool}$ in the catalyst bed

| | $T_{cool}/°C.$ | | | | $X_{tot}(CO_x)/$ | STY(MeOH)/ kg/(h |
|---|---|---|---|---|---|---|
| Case | 1st stage | 2nd stage | 3rd stage | 4th stage | % total | $l_{cat}$) total |
| Reference | 220 | 220 | 220 | 220 | 95.1 | 1.53 |
| 3 | 200 | 220 | 240 | 260 | 89.4 | 1.44 |
| 4 | 260 | 240 | 220 | 200 | 96 | 1.55 |

TABLE 5

Variation in the condensation temperature $T_{cond}$

| | $T_{cond}/°C.$ | | | | Cooling output/ | $CO_2$ losses/ |
|---|---|---|---|---|---|---|
| Case | 1st stage | 2nd stage | 3rd stage | 4th stage | MW total | % total |
| Reference | 40 | 40 | 40 | 40 | 39.9 | 7.4 |
| 5 | 100 | 80 | 60 | 40 | 33.7 | 3.7 |
| 6 | 40 | 60 | 80 | 100 | 34.9 | 6.0 |

INDUSTRIAL APPLICABILITY

The invention proposes a reactor for conducting exothermic equilibrium reactions, especially for the performance of the methanol synthesis by heterogeneously catalysed conversion of synthesis gas, which enables readjustment and hence optimization of the reaction conditions along the longitudinal coordinate of the reactor, which, for example in the case of the methanol synthesis, leads to a reduction in the recycle ratio to smaller values as known in the case of use of the reactors known from the prior art. Corresponding recycle conduits, circulation compressors etc. can therefore have a smaller configuration, or it may be possible to dispense with them entirely. This reduces the corresponding capital costs.

The optimization of the reaction conditions along the longitudinal coordinate of the reactor also reduces the formation of unwanted by-products, which affords a purer target product and reduces the complexity of purification.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

LIST OF REFERENCE NUMERALS

[1] reactor
[2] reactor shell
[3] reaction cell
[10] conduit
[20] preheating zone
[22] conduit
[24] heat exchanger
[26] conduit
[28] conduit
[30] reaction zone
[31] catalyst bed
[32] conduit
[33] catalyst bed
[34] heat exchanger
[35] conduit
[36] conduit
[38] conduit
[40] first cooling zone
[42] conduit
[44] heat exchanger
[46] conduit
[47] conduit
[48] conduit
[50] second cooling and deposition zone
[51] deposition apparatus
[52] conduit
[53] conduit
[54] heat exchanger
[56] conduit
[60] conduit
[70] steam generator
[78] conduit

The invention claimed is:

1. A reactor for conducting exothermic equilibrium reactions, in which a gaseous feed mixture is at least partly converted over a solid catalyst to a product mixture comprising at least one liquid reaction product condensable at a reactor pressure and at temperatures below a reactor temperature, the reactor comprising at least two series-connected reaction cells that are in fluid connection with one another and are arranged in a common reactor shell, wherein each reaction cell comprises the following series-connected assemblies that are in fluid connection with one another:
   (a) a preheating zone suitable for heating the feed mixture or the gaseous product stream from the upstream reaction cell, wherein the preheating zone can optionally be dispensed with in the first reaction cell in flow direction of the gaseous feed mixture;
   (b) at least one reaction zone comprising a catalyst active in respect of the exothermic equilibrium reaction to be conducted and a cooling apparatus in a heat-exchanging relationship with the catalyst;
   (c) at least one cooling zone comprising a cooling apparatus suitable for cooling the partly converted, gaseous product stream that has been laden with condensable reaction product and exits from the reaction zone to a temperature below the dew point of this gas;
   (d) a deposition zone comprising a phase separation apparatus for separation of the product stream that exits from the cooling zone into a gaseous product stream that has been freed of condensate and a condensate stream comprising liquid reaction product;
   (e) means of discharging the condensate stream comprising liquid reaction product; and
   (f) means of discharging the gaseous product stream that has been freed of condensate and means of feeding this gaseous product stream to a subsequent reaction cell arranged downstream and/or means of discharging the gaseous product stream from the reactor.

2. The reactor according to claim 1, wherein the cooling zone comprises the following in assembly (c):
   (c1) a first cooling zone comprising a cooling apparatus suitable for cooling the partly converted, gaseous product stream that has been laden with condensable reaction product and exits from the reaction zone to a temperature below the temperature in the reaction zone; and
   (c2) a second cooling zone comprising a cooling apparatus suitable for further cooling the partly converted, precooled gaseous product stream that has been laden with condensable reaction product and exits from the first cooling zone to a temperature below the dew point of this gas.

3. The reactor according to claim 1, wherein the shell is arranged horizontally or vertically with respect to the perpendicular imparted by gravity, wherein the flow of the gaseous feed mixture or the gaseous product stream from the upstream reaction cell through the reaction cells in both cases is vertical.

4. The reactor according to claim 1, wherein the shell is arranged horizontally or vertically with respect to the perpendicular imparted by gravity, wherein the flow of the gaseous feed mixture or the gaseous product stream from the upstream reaction cell through the reaction cells in both cases is horizontal.

5. The reactor according to claim 4, wherein the shell is arranged vertically with respect to the perpendicular imparted by gravity, wherein the flow of the gaseous feed mixture or the gaseous product stream from the upstream reaction cell through the reaction cells is horizontal and in radial direction.

6. The reactor according to claim 2, wherein the preheating zone (a) and the first cooling zone (c1) coincide spatially or functionally and are in a heat-exchanging relationship with one another.

7. The reactor according to claim 1, wherein the reaction zone (b) has been equipped with thermoplates, wherein the thermoplates consist of two sheets each bonded to one another, wherein this composite has, on its inside, a cavity which is tightly sealed from the outside and through which a fluid cooling medium flows, wherein the catalyst is present in the reaction zone in piece form or particulate form as a bed of solid material arranged between two adjacent thermoplates in each case in such a way that the gaseous feed mixture or the gaseous product stream from the upstream reaction cell can flow through it vertically or horizontally, and wherein the catalyst and the cooling medium are in an indirect heat-exchanging relationship.

8. The reactor according to claim 1, wherein the preheating zone, the reaction zone or the cooling zones or two or more of these assemblies are executed in the form of a lamellar heat exchanger.

9. The reactor according to claim 1, wherein the cooling medium used is hot condensate from a steam generator, wherein the cooling medium takes up at least a portion of the heat of reaction released in the reaction zone (b) and is partly evaporated, and wherein the condensate/saturated steam mixture obtained or the saturated steam is at least partly recycled to the steam generator and/or conducted as heat carrier to the preheating zone (a) of the same reaction cell.

10. The reactor according to claim 1, wherein means are encompassed which permit at least partial recycling of the condensate/saturated steam mixture removed from one or more reaction cells or of the steam component only to a steam generator and at least partial release of the saturated steam drawn off from the steam generator as export steam to external consumers.

11. The reactor according to claim 1, wherein means are encompassed which permit, in the preheating zone (a), the heating of the feed mixture or of the gaseous product stream from the upstream reaction cell in indirect heat exchange against hot condensate from a steam generator, to obtain a cooled hot condensate stream.

12. The reactor according to claim 1, wherein means are encompassed which permit supply of the cooled hot condensate stream from the first cooling zone (c1), removed from the preheating zone (a), as cooling medium in a preceding reaction cell arranged upstream, followed by recycling thereof to a steam generator.

13. The reactor according to claim 1, wherein at least some of the cooling zones and/or preheating zones are configured as plate heat exchangers with thermoplates.

14. The reactor according to claim 1, wherein means are encompassed which permit supply of fresh feed mixture that has not yet been partly converted or individual reactants to one or more of the subsequent reaction cells arranged downstream of the first reaction cell.

15. The reactor according to claim 1, wherein the reaction zone (b) is equipped, in at least one reaction cell, with at least two catalysts having different activity with regard to the exothermic equilibrium reaction.

16. The reactor according to claim 1, further comprising means of feeding the condensate stream to a workup apparatus for the reaction product.

17. A process for preparing methanol, the process comprising the steps of providing the reactor according to claim 1; and converting a carbon dioxide-containing synthesis gas feed to methanol using the reactor.

* * * * *